United States Patent [19]

Kowalski

[11] Patent Number: 4,499,540

[45] Date of Patent: Feb. 12, 1985

[54] DEVICE FOR THE TESTING OF BODIES COMPRISING PERIODIC STRUCTURES

[75] Inventor: Günter Kowalski, Pinneberg, Fed. Rep. of Germany

[73] Assignee: U.S. Philips Corporation, New York, N.Y.

[21] Appl. No.: 362,019

[22] Filed: Mar. 25, 1982

[30] Foreign Application Priority Data

Mar. 31, 1981 [DE] Fed. Rep. of Germany ....... 3112758

[51] Int. Cl.³ ............................................ G01N 23/00
[52] U.S. Cl. .................................. 364/414; 364/485; 378/58; 378/98
[58] Field of Search ....................... 364/507, 485, 414; 378/14, 58, 62, 98, 145, 147

[56] References Cited

U.S. PATENT DOCUMENTS

| | | | |
|---|---|---|---|
| 4,211,926 | 7/1980 | Nakaya et al. | 378/98 X |
| 4,213,183 | 7/1980 | Barron et al. | 364/507 |
| 4,293,912 | 10/1981 | Wlaters | 364/414 |
| 4,321,680 | 3/1982 | Bertrand et al. | 364/485 |
| 4,326,252 | 4/1982 | Kohno et al. | 364/414 |
| 4,394,738 | 7/1983 | Wagner | 364/414 |
| 4,415,980 | 11/1983 | Buchanan | 378/58 |

Primary Examiner—Edward J. Wise
Attorney, Agent, or Firm—Paul R. Miller

[57] ABSTRACT

The invention relates to a device for testing a body which comprises periodic structures. The device includes an image forming device for determining measurement signals representing the periodic structures, and a further electronic device. This electronic device forms the frequency spectrum from neighboring measurement values in the direction of the periodic body structures, suppresses the fundamental and higher harmonics ($G, B_1, B_3$) of the periodic structures in the relevant spectrum, and retransforms the spectrums thus modified for application to an image evaluation device.

7 Claims, 4 Drawing Figures

DEVICE FOR THE TESTING OF BODIES COMPRISING PERIODIC STRUCTURES

The invention relates to a device for the testing of a body comprising periodic structure, said device comprising an image forming device which scans the structure of the body and which supplies measurement values, an electronic device for the processing of the measurement values, and a display device for the display of information derived from the measurement values.

Devices of this kind are generally known. They are used inter alia for examining bodies for internal or external faults. For non-destructive testing of materials, devices of this kind are used for the measurement of, for example, gas inclusions in moulded products or other faults in the body structure which have an adverse affect on the mechanical strength of workpieces.

To this end, either the bodies are irradiated, for example, by means of X-rays or ultrasonic radiation or the like, or the surfaces thereof are scanned by means of electro-mechanical means. Thus, an image is made of the body with the faults for observation by an inspector or an automatic image recognition unit in order to determine the faults.

The body images to be observed, however, are comparatively, obscure, so that it is difficult to recognize the structures containing the faults. This is even the case for bodies or workpieces which themselves are not obscure because of the periodic body structures.

It is an object of the invention to provide a device whereby the rcognizability of faults in bodies comprising a periodic structure is improved.

To this end, the device in accordance with the invention is characterized in that the electronic device forms the frequency spectrum of the neighbouring measurement values in the direction of the periodic body structure by means of a Fourier transformation device, suppresses the fundamental and higher harmonics of the periodic structure in the frequency spectrum thus determined, and retransforms the frequency spectrum thus modified into a spatial structure to be supplied to the image display device or an automatic image recognition unit, an output signal of which is applied to the display device.

For example, when the body to be examined is irradiated or the image thereof is stored in a storage matrix so that the body periodicities are situated in the direction of the rows of the matrix, the measurement or image values each time situated on a memory row form an image signal. The spectrum of the image signal which is associated with a memory row and which represents, for example, a periodic or non-periodic function of the body absorption or the like, is then obtained by means of a Fourier transformation. After supperssion of the fundamental and higher harmonics in the frequency spectrum which represent the periodic or monotonous body structures, the spectrum thus modified is line-wise retransformed. Obviously, the Fourier transformation can alternatively be performed in a direction other than the row direction, or also two-dimensionally. This is advantageous notably if the body comprises periodic structures in mutually perpendicular directions.

The device in accordance with the invention thus enables a substantial reduction of the information content of the image of a periodic body. Thus, only the material faults or production faults or other non-periodic details of the body remain in the body image. The evaluation of the body image by a human observer for example, on a monitor is thus substantially facilitated; the image can also be applied to an automatic image recognition or evaluation unit which produces a fault indication in the presence of a fault structure or an excessive number of faults.

Two feasible examples of image processing will be described hereinafter. The workpiece is, for example, a very accurately manufactured worm wheel of which an image is formed which contains the periodicities thereof and which is Fourier transformed in the direction of the worm wheel periodicities. A subsequent elimination of the periodic and the similar parts should cause a complete disappearance of the image of the worm wheel; otherwise a fault is present. In this case the evaluation unit merely has to count the image points below a negative threshold value (=lacking material) and this unit classifies the workpiece as containing faults when such image points occur too frequently. The image point exceeding a positive threshold value can also be detected (=excess material at the surface), in which case it may be necessary to subject the workpiece to further treatement.

For other applications where the exact type and position of the fault must be evaluated by a human observer, the occurrence of a non-periodic structure can be displayed in a signal colour on a colour monitor, so that the recognizability of the fault is enhanced.

The drawing shows embodiments in accordance with the invention.

Figure 1:
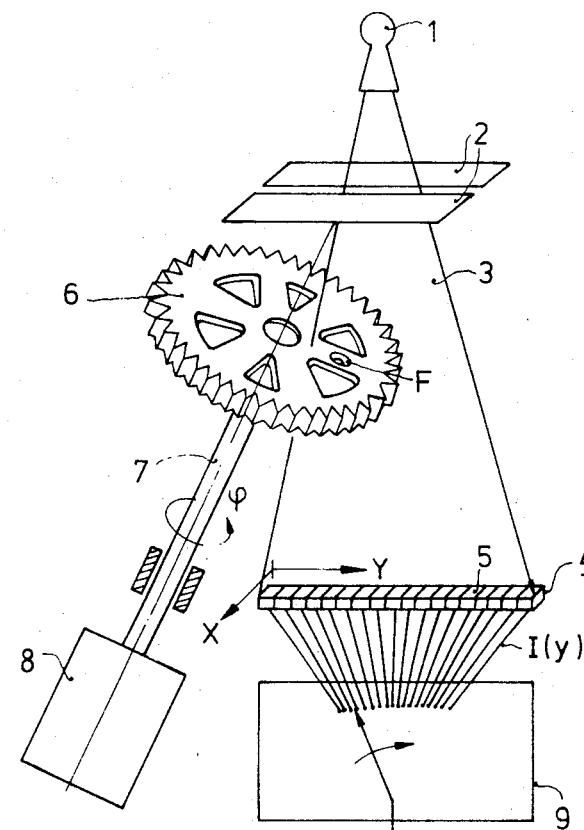
FIG. 1 shows a device in accordance with the invention with a fan-shaped X-ray beam and a periodic workpiece to be irradiated.
Figure 1:
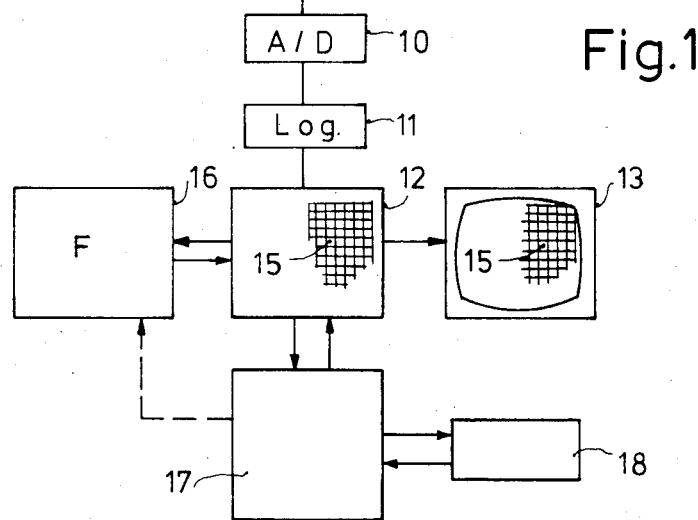

FIG. 1 shows a device in accordance with the invention which comprises an X-ray source 1 whose X-rays are collimated by means of a slit diaphragm 2 in order to form a flat, fan-shaped radiation beam 3. The radiation beam 3 is incident on a detector array 4 which is situated in the plane thereof and which consists of a large number of separate detectors 5, for example, 512 detectors, which produce electronic measurement signals $I(y)$ on their output in accordance with the incident X-rays. The variable y indicates the location of a detector 5 on the coordinate axis Y which extends parallel to the detector array 4. The radiation source 1, the slit diaphragm 2 and the detector array 4 constitute the image forming device.

The workpiece to be examined is shown, by way of example, as a gearwheel 6 which is mounted on a shaft 7 and which is rotated through an angle $\phi$ by means of a drive 8. The radiation beam 3 then irradiates the gearwheel 6 in radial direction, so that by rotation of the gearwheel 6 through the angle $\phi = 360°$, a complete image A is obtained in a $\phi - Y$ coordinate system if for each angle $\phi$ the measurement values measured by means of the detector array 4 at this angle $\phi$ or the image values derived therefrom are imaged in the direction of a coordinate axis $\phi$ which extends perpendicularly to the Y axis. The measurement values $I(y)$ are applied, via a multiplexer 9, to an analog-to-digital converter 10 and subsequently to a logarithm-forming device 11 for obtaining the image values representing the attenuation of the X-rays. This image A can be stored in a memory 12, for example, in a matrix memory and be displayed on a monitor 13.

Figure 2:
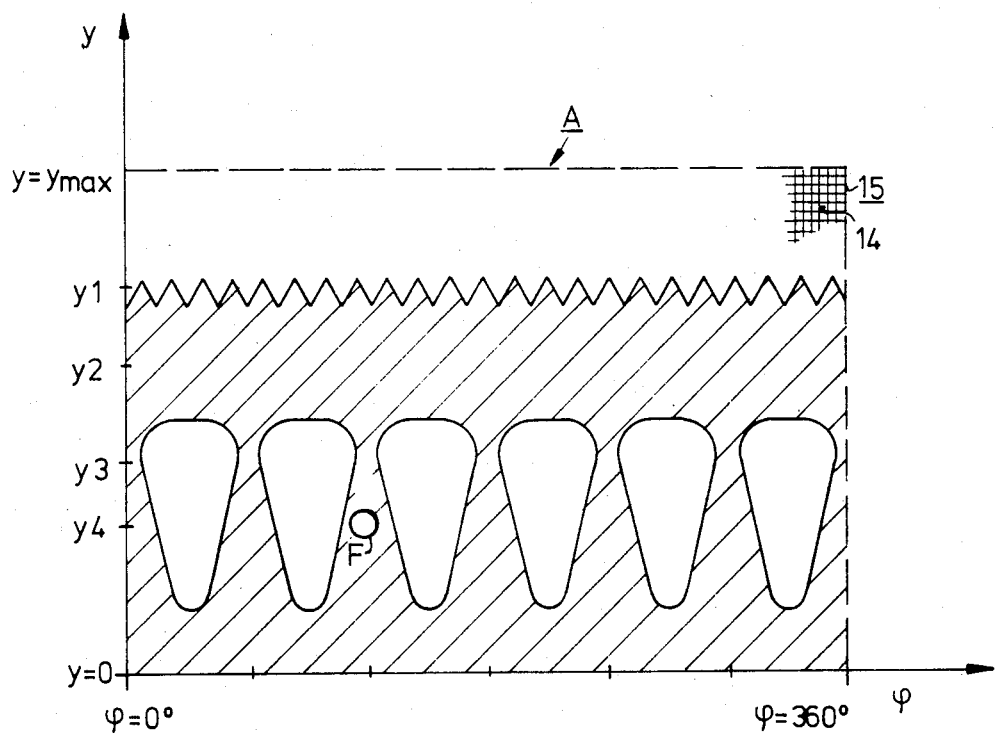
FIG. 2 shows an image with the periodic structures of the workpiece.

FIG. 2 shows the image A of the gearwheel 6 in a memory matrix 15 consisting of separate memory elements 14 which are arranged in rows and columns. On the abscissa there is plotted the coordinate direction or the angle of rotation $\phi$ and on the ordinate there is plotted the coordinate direction Y. The image A is an image in which the (periodic) structures of the gearwheel 6 are present which extend in the direction of the matrix rows. In the zone around the value y1, each time extending in the row direction, the periodic structures of the teeth of the gearwheel 6 are situated, while in the zone y3 the periodic spoke structure is visible. In the zone y2, the image A has a monotonous structure, i.e. the image values do not change to any extent in the line direction ($\phi$).

A fault F which is present in a spoke of the gearwheel 6 shown in FIG. 1, for example, a cavity (trapped gas bubble) which reduces the strength of the gearwheel 6 also appears in the image A, that is to say in the zone y4. In this zone y4 the image A exhibits periodic as well as non-periodic structures in the $\phi$ direction. The image signals originating from the measurement values or image values of the memory elements 14 in the $\phi$ direction, therefore, are also periodic in the zones y1 and y3 and monotonous in the zone y2. However, in the zone y4, the image signals consist of periodic and non-periodic image signals portions.

Figure 3:
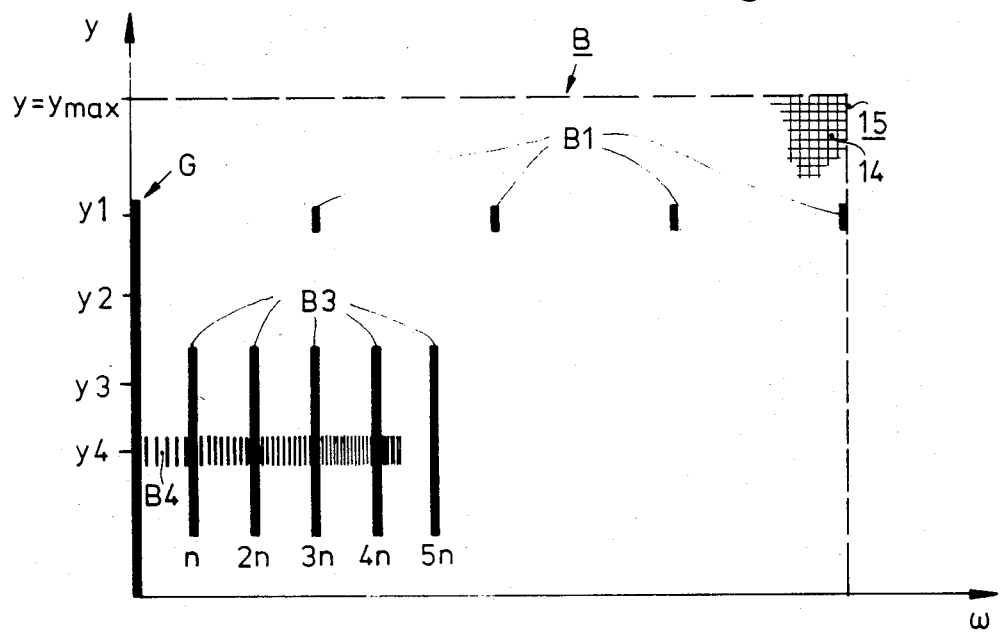
FIG. 3 shows the frequency spectrum of the workpiece image which has been Fourier transformed in the direction of the periodic structures.

The image signals are Fourier transformed one line after the other, each time for a constant y. As appears from FIG. 1, there is provided a Fourier transformation element 16 which is connected to the memory 12 and which operates under the control of a computer 17 which is also connected to the memory 12. For each value of y, the Fourier transform is determined for the series of image values associated with all values $\phi$. Thus, for each value of y a frequency spectrum is formed. The Fourier transformed spectrum image B which is shown in FIG. 3 and which consists of amplitude spectrums of the frequency signals exhibits the amplitudes of the separate spectral portions of the relevant image signals in different grey values (image values). The spectrum image B (or information field) comprises, in addition to the portions G associated with the frequency zero, a typical, substantially discrete band spectrum B1, B3 in zones containing periodic structures y1 and y3.

The frequency position of these band B1 and B3 in the relevant zones y1 and y3, respectively, is determined inter alia by the number of periods n and by an integer number N=1, 2, 3, etc., that is to say by the product n.N. In the case of a single scan of the gearwheel the signal in the spoke zone comprises, for example, 6 periods which cause the frequencies 6, 12, 18, 24, etc., while at the area of the teeth (zone y1) the number of periods n is substantially larger (n=25).

Furthermore, in the zone y4 the spectrum image B has a substantially continuous spectrum B4 which represents the non-periodic fault F and which is superposed on the discrete spectrum B3.

In order to increase the recognizability of the fault F in the image A shown in FIG. 2, all fundamental and higher harmonics thereof are suppressed, in the Fourier transformed spectrum image B, that is to say the portions G (signal portions having the frequency $\omega=0$) and the bands B1 and B3.

If the number of periods n is known (in the spoke zone y3, n=6, see FIG. 1) and if the periodic or the monotonous body zones are also known in advance such as is the case, for example, with completely known workpieces, the frequencies and the width of the bands B1 and B3 in the y-direction in the spectrum image B can be directly determined by means of the computer 17. The band B1 and B3 can then be directly suppressed, the values of the image elements 14 of a memory matrix 15, which correspond to the frequency bands then being adapted to the value of the environment, taking into account the (frequency) width. It must be ensured that at the transitions between zones containing periodic structures and zones containing monotonous or non-periodic structures, the suppression of the band spectrum takes place with a slowly decreasing weight and not too abruptly, so that no periodic absence of frequencies in the spectrum arises. Otherwise non-existing periodic structures would arise upon retransformation to the spatial domain.

Figure 4:
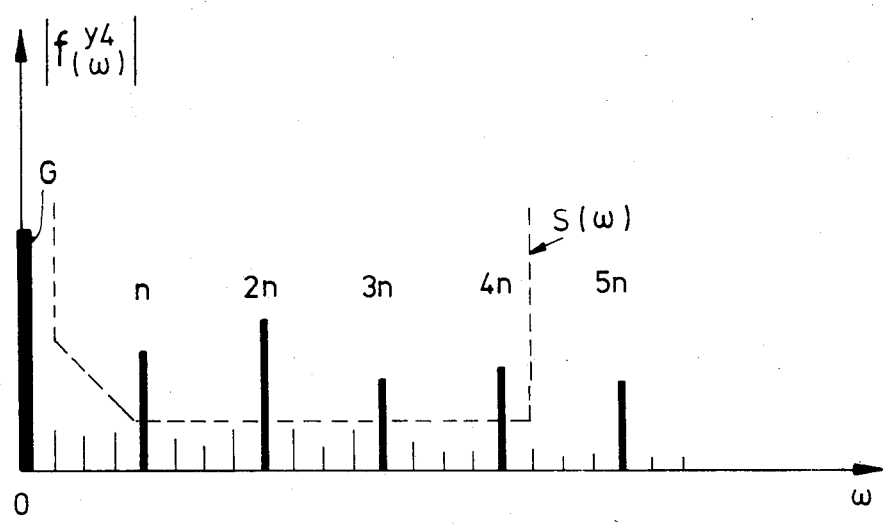
FIG. 4 shows a part of the frequency spectrum of FIG. 3.

The domains of the band B1 and B3 and the monotonous body zones, however, can also be determined on the basis of the Fourier transformed image 3 and by means of the computer 17. Generally, it will be sufficient to search the Fourier spectrum with a simple threshold value $S(\omega)$. To this end, the absolute amplitudes of the Fourier components f are fetched each time for a value of y (for example, y4) for comparison with a threshold value $s(\omega)$. FIG. 4 shows the Fourier components $f_{(\omega)}y4$ as a function of the frequency in the zone y4 (see FIG. 3), a broken line indicating the (frequency-dependent) threshold value $S(\omega)$.

When the threshold value $S(\omega)$ is correctly chosen, possibly in a frequency-dependent manner, the spectrum exceeds this threshold value for the first time at the frequency n (and sometimes at the associated frequency $\omega n$ of the higher harmonics). When this period n has been measured, all frequency components, the fundamental harmonic n and higher harmonics 2n, 3n etc. are also suppressed, because the periodicity generally is not sinusoidal. The process can be repeated when the frequency spectrum contains several fundamental harmonics and associated higher harmonics. If not one component $n \geq 1$ exceeds the threshold value, the workpiece is monotonous. The threshold value can be determined, for example, empirically. However, it can also be chosen to be proportional to the total energy of the signal $$E = \sqrt{\Sigma |f^2|}.$$

for example, in order to be adapted to different parts of the spectrum.

When the fundamental and higher harmonics (G and the bands B1 and B2) have been suppressed, the remaining frequency spectrum thus modified is applied to the Fourier processor 16 and is line-wise retransformed. The body image A' thus formed and made visible, for example, on the monitor 13, contains no periodic or regular structures and hence little dynamics, because the periodic and monotonous body structures are substantially no longer present therein. An observer or an automatic image recognition unit 18 which is connected to the memory 12 directly or via the computer 17 and which receives the retransformed image signals therefrom can thus readily recognize any materials faults present.

Obviously, the image forming device shown in FIG. 1 is also suitable for the testing of other periodic workpieces. For example, a shadow image of a worm shaft (not shown) in which the periodic worm shaft structures are present can be obtained by rotating the worm shaft in the direction of its longitudinal axis and perpendicularly to the plane of the fan 3 ($\phi$-direction). During this operation, the worm shaft may be arranged, for example, on a conveyor belt.

The image forming device, however, may alternatively have a spatially diverging X-ray beam which is incident on a two-dimensional detector array with local resolution. Such an image forming device enables the complete irradiation of workpieces in a shorter period of time.

It is also possible to form the image forming device as an ultrasonic transducer so that, using ultrasonic waves, an image of a body can be formed in which the periodic structures are present.

If only the periodic surface of a body is to be examined for cracks of notches, use can also be made of an electromechanical system which scans only the surface, thus forming a body image containing the body periodicity.

I claim:
1. A device for testing a body having a periodic structure comprising:
    image forming means for scanning a body structure and supplying measurement values, said image forming means including an array of separate detectors producing electric signals representative of said measurement values,
    electronic means for processing said measurement values,
    said electronic means including Fourier transformation means for forming a frequency spectrum of neighboring measurement values in a direction of said periodic structure, first means for suppressing fundamental and higher harmonics ($G, B_1, B_3$) of said periodic structure in said frequency spectrum, and second means for retransforming said frequency spectrum thus modified into a spatial structure; and
    display means for displaying information derived from said measurement values, said display device receiving a signal from said second means.

2. A device according to claim 1, wherein an automatic image recognition means receives said signal from said second means and applies an output signal to said display means.

3. A device according to one of claims 1 or 2, wherein said image forming means includes an X-ray source, and wherein said array of detectors are location sensitive detectors.

4. A device according to claim 3, wherein a stop is placed relative to said X-ray source to form a flat fan-shaped beam.

5. A device according to one of claims 1 or 2, wherein said image forming means includes an ultrasonic transducer.

6. A device according to one of claims 1 or 2, wherein said image forming means includes an electromechanical means for scanning a surface of said body structure.

7. A device according to one of claims 1 or 2, wherein said array of detectors includes 512 detectors situation in a plane and arranged in a row adjacent one another.

* * * * *